United States Patent [19]

Isaacson et al.

[11] Patent Number: 5,152,788
[45] Date of Patent: Oct. 6, 1992

[54] MULTIFOCAL DIFFRACTIVE OPHTHALMIC LENS AND METHOD OF MANUFACTURE

[75] Inventors: William B. Isaacson; John A. Futhey; Kent D. Thompson; Paul T. Ihn, all of St. Paul, Minn.

[73] Assignee: Minnesota Mining and Manufacturing Company, St. Paul, Minn.

[21] Appl. No.: 456,679

[22] Filed: Dec. 27, 1989

[51] Int. Cl.⁵ .................. A61F 2/16; B32B 31/16; G02B 5/18; A61M 35/00

[52] U.S. Cl. .................... 623/6; 156/73.1; 359/565; 604/294

[58] Field of Search ............... 351/160 H, 160 R, 161, 351/162; 604/294; 623/6; 156/73.1; 219/121.6; 359/565

[56] References Cited

U.S. PATENT DOCUMENTS

| | | | |
|---|---|---|---|
| 3,630,200 | 12/1971 | Higuchi | 128/260 |
| 4,210,391 | 7/1990 | Cohen | 351/161 |
| 4,338,005 | 7/1982 | Cohen | 351/161 |
| 4,340,283 | 7/1982 | Cohen | 351/161 |
| 4,575,372 | 3/1986 | Gundersen | 623/6 |
| 4,618,649 | 10/1986 | Ofstead | 525/60 |
| 4,637,697 | 1/1987 | Freeman | 351/161 |
| 4,641,934 | 2/1987 | Freeman | 351/159 |
| 4,642,112 | 2/1987 | Freeman | 623/6 |
| 4,655,565 | 4/1987 | Freeman | 351/159 |
| 4,664,666 | 5/1987 | Barrett | 623/6 |
| 4,685,921 | 8/1987 | Peyman | 623/6 |
| 4,685,922 | 8/1987 | Peyman | 623/6 |
| 4,693,939 | 9/1987 | Ofstead | 428/421 |
| 4,702,865 | 10/1987 | Koziol et al. | 264/17 |
| 4,704,016 | 11/1987 | de Carle | 351/161 |
| 4,731,078 | 3/1988 | Stoy et al. | 623/6 |
| 4,771,089 | 9/1988 | Ofstead | 524/41 |
| 4,828,558 | 5/1989 | Kelman | 623/6 |
| 4,846,833 | 7/1989 | Cumming | 623/6 |

FOREIGN PATENT DOCUMENTS

| | | |
|---|---|---|
| 43640 | 1/1982 | European Pat. Off. . |
| 1154360 | 6/1969 | United Kingdom . |
| 2171106 | 8/1986 | United Kingdom . |

OTHER PUBLICATIONS

O. Wichterle, "Hydrogels," *Encyclopedia of Polymer Science and Technology*, vol. 15, 1971, pp. 273-291.

Wichterle et al., "Hydrophilic Gels for Biological Use," *Nature*, 185:117-118, 1960.

Ratner et al., "Synthetic Hydrogels for Biomedical Applications," *Hydrogels for Medical and Related Applications*, Am. Chem. Soc., Wash, D.C., 1976, pp. 1-35.

R. A. Clarke, "Ultrasonic Assembly," *Modern Plastics Encyclopedia*, 1980-81, pp. 447-451.

Jordan et al., "Kinoform Lenses," Aug. 1970, *Applied Optics*, pp. 1883-1887.

*Primary Examiner*—Scott J. Sugarman
*Attorney, Agent, or Firm*—Gary L. Griswold; Walter N. Kirn; Walter C. Linder

[57] ABSTRACT

A multifocal ophthalmic lens includes first and second lens members. Each lens member has a smooth outer surface and an inner surface with an edge about its perimeter. A multifocal diffractive zone plate on at least one of the lens members is characterized by an index of refraction. The lens members are joined at the edges by ultrasonic welding to form a cavity adjacent the diffractive zone plate. The cavity is filled with a liquid medication having an index of refraction which is different than the index of refraction of the diffractive zone plate. A hole through one of the lens members functions as a fluid transport mechanism to permit transfer of the medication between the cavity and eye.

35 Claims, 4 Drawing Sheets

MULTIFOCAL DIFFRACTIVE OPHTHALMIC LENS AND METHOD OF MANUFACTURE

CROSS-REFERENCE TO COPENDING APPLICATION

Reference is hereby made to copending application, U.S. Ser. No. 07/456,680, filed Dec. 27, 1989, entitled ULTRASONICALLY WELDED HYDROGEL OPHTHALMIC LENS.

FIELD OF THE INVENTION

The present invention relates to diffractive multifocal ophthalmic lenses.

BACKGROUND OF THE INVENTION

Ophthalmic lenses used to correct vision impairments can be embodied in a number of forms. Contact lenses and surgically implanted intraocular lenses are probably the most common. Other ophthalmic lenses include artificial corneas and intralamellar implants. Ophthalmic lenses having a single focal length, those used to correct vision problems within only one general distance range (e.g. nearsightedness or farsightedness) are disclosed in a number of United States patents.

The Kelman U.S. Pat. No. 4,828,558 is directed to a composite lens formed by a pair of relatively thin, sheet-like elements having opposed interior surfaces. At least one of the elements includes a protected Fresnel lens on its interior surface. The interior surfaces are sealed together to define gas enclosing, liquid free spaces having an index of refraction which is different from that of the elements. The Fresnel lens includes a succession of concentric rings and uses the principle of refraction to produce the desired optical correction.

The Stoy et al. U.S. Pat. No. 4,731,078 discloses an intraocular lens formed by inner and outer layers. The inner layer can be formed by a gas or liquid filled cavity. Alternatively, the inner layer can have a Fresnel-like interface which can be gas filled.

Day-to-day activities require in-focus vision for both long and short distances (e.g. for driving and reading). Healthy human eyes provide the variable focal length capabilities needed for this range of vision by muscle-induced distortions of its flexible lens. Unfortunately, the ability of the eye to accommodate variable distance vision commonly deteriorates with age. The ability to accommodate multiple focal lengths through muscle distortions of the lens is also limited for those persons with known surgically implanted replacement lenses. Multifocal lenses, those having several predetermined focal lengths, are therefore used where correction is needed for both short and long distance vision.

The Hofmann United Kingdom Patent No. 1,154,360 discloses a multifocal Fresnel lens. In one embodiment the Fresnel lens is formed on an internal face, adjacent an airfilled space.

The use of multifocal diffractive zone plates in ophthalmic lenses is also known and disclosed in the Cohen U.S. Pat. Nos. 4,210,391, 4,338,005 and 4,340,283. These lenses use the principle of diffraction to provide the optical power. A plurality of concentric annular regions direct light to multiple focal points. The unfocused image does not affect the focused image.

The Higuchi U.S. Pat. No. 3,630,200 discloses an ocular insert. The insert is positioned between the eyeball and eye lid, and dispenses drugs to the eye over a prolonged period of time. The insert can be fabricated of an inner core containing the drug and a soft hydrophilic outer layer.

The Tahan U.K. Patent Application Publication 2,171,106 discloses hydrogel forming polymers for contact and intraocular lenses. It is noted that the polymers can be formed into a bandage lens for an eye and drugs such as antibiotic substances can be incorporated into the lens for gradual diffusion into the eye.

High quality vision is very important to most people. However, vision impairments which require correction for both long and short distances are relatively common. There is, therefore, a continuing need for improved multifocal ophthalmic lenses. Lenses of this type must be capable of providing accurate vision correction. The lenses should also be physiologically compatible with the human eye for long-term comfort, and convenient to use.

SUMMARY OF THE INVENTION

The present invention is a multifocal ophthalmic lens which offers a high degree of compatibility with the physiology of the human eye. The lens includes first and second lens members, each having a smooth outer surface and an inner surface with an edge about its perimeter. A multifocal diffractive zone plate on the inner surface of the first lens member is characterized by an index of refraction. The edges of the lens members are fixedly joined to form a cavity defined by the inner surfaces and adjacent the diffractive zone plate. The cavity is characterized by an index of refraction which is different than the index of refraction of the diffractive zone plate.

One embodiment of the lens includes an ultrasonic weld for joining the edges of the lens members. Another embodiment includes adhesive for joining the edges.

Still other embodiments of the lens include a liquid medication within the cavity. A fluid transport mechanism such as an aperture through one of the lens members permits the medication to be transferred between the cavity and eye.

DETAILED DESCRIPTION OF THE PREFERRED EMBODIMENTS

Figure 1:
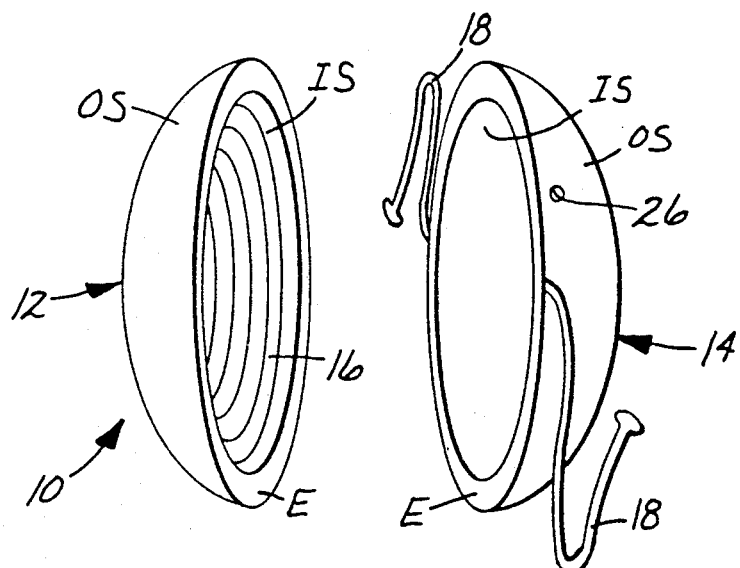
FIG. 1 is an exploded view of a first embodiment of an ophthalmic lens in accordance with the present invention.
Figure 2:
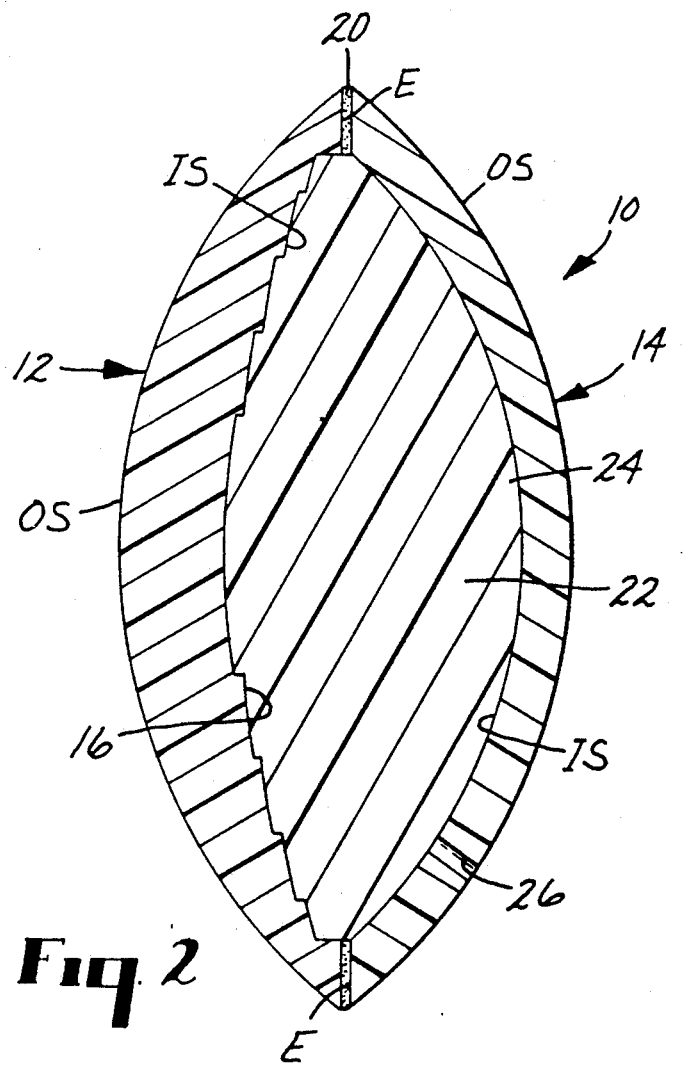
FIG. 2 is a sectional view of the lens shown in FIG. 1.

Ophthalmic lens 10, a first embodiment of the present invention, is illustrated generally in FIGS. 1 and 2. As shown, lens 10 includes a first lens member 12 and a second lens member 14. Lens members 12 and 14 both have a smooth outer surface OS and an inner surface IS. The inner surfaces IS of lens members 12 and 14 terminate at annular edges E that extend around the perimeter of the lenses. A multifocal diffractive zone plate 16 is formed on the inner surface IS of one or both lens members 12 and 14, and is shown on lens member 12 in FIG. 1. Lens 10 can also include haptics 18 if it is designed to be surgically implanted. The diameter of the body of lens 10 (i.e., the portion exclusive of haptics 18) is typically in the range of 7.0 to 7.5 mm for implantable lenses, but can vary from this range as required for any particular application.

Edges E function as bonding surfaces. As shown in FIG. 2, lens members 12 and 14 are fixedly joined together at their edges E. An adhesive 20 can be used for this purpose. In another embodiment described below, the lens members are ultrasonically welded together. Alternatively, lens members 12 and 14 can be affixed by mechanical interlocks on edges E, by solvent welding or by heat lamination processes (not shown). Once lens members 12 and 14 have been joined together, their inner surfaces IS form and define a chamber or cavity 22. Cavity 22 is adjacent diffractive zone plate 16 and can be filled with a substance or material 24 as shown in FIG. 2. Alternatively, lens 10 can be formed with a vacuum in cavity 22.

Multifocal diffractive zone plate 16 can be of any known or conventional design. In the embodiment shown in FIGS. 1 and 2, zone plate 16 is formed by physical structures on the inner surface IS of lens member 12. Alternatively, diffractive zone plate 16 could be formed by doping portions of lens member 12 with a dopant that causes the index of refraction of the doped regions to change and be different from that of adjacent portions of the lens member and cavity 22. The optical power of lens 10 is produced by the combination of the diffractive contribution from zone plate 16 and any refractive contribution from lens members 12 and/or 14.

Lens members 12 and 14 can be fabricated from a number of different materials. Examples of relatively impermeable materials can include polymethylmethacrylate (PMMA), silicone acrylate and perfluorinated polyethers. Alternatively, hydrophilic or water-containing materials such as silicones and hydrogels can be used. Specific hydrogels include homopolymers and copolymers of acrylate and methacrylate esters having at least one hydroxyl group on the side chain, such as 2-hydroxyethyl methacrylate (HEMA), ethylene glycol dimethacrylate, hydroxyethoxyethyl methacrylate, hydroxydiethoxy methacrylate, and glyceryl methacrylate, as well as polymers and copolymers of monomers such as methoxyethoxyethyl methacrylate, methoxydiethoxyethyl methacrylate, methoxyethyl methacrylate, methacrylic acid, vinyl alcohol, vinyl acetate, and N-vinyl-2-pyrrolidone and related N-alkenyl-2-pyrrolidones. Cross-linked hydrogels can also be used.

Materials of these types typically have an index of refraction in the range of 1.43 to 1.5. To enable the operation of a structured diffractive multifocal zone plate 16, the index of refraction of the vacuum or material 24 within central cavity 22 must differ from the index of refraction of adjacent inner surface IS on which the zone plate is formed. If the differences between the indices of refraction are relatively large (e.g. greater than 0.1), the physical dimensions of the surface structure of zone plate 16 will be relatively small (e.g. peak-to-valley dimensions of two micrometers). While this reduces the overall dimensional thickness of the lens member in which the zone plate is formed, it makes it more difficult to manufacture the zone plate to required tolerances. If the difference between the indices of refraction are smaller, for example in the range of 0.04 to 0.07, surface structures with peak-to-valley dimensions in the range of seven micrometers can be used. These larger surface structures can more easily be manufactured to the required dimensional tolerances.

Cavity 22 can be filled with solid or fluid materials 24. Ultraviolet and "air" cured polymers can be used for solid materials 24. Examples include 3M materials Acylamidoamidosiloxane (ACMAS) and Methacylamido Amido Siloxane (MACMAS), and Dow Corning compounds Sylgard 182 and Silastic Q-7485 A/B. Gases such as air or biologically benign liquids such as saline solution can also be used. Saline solution having properly selected characteristics is a desirable material since it is compatible with and has the same index of refraction as fluids in the human eye.

Cavity 22 can also be filled with medications for treating portions of the eye adjacent lens 10. For applications of this type, lens 10 must include a fluid transport mechanism for transferring the medication between cavity 22 and the eye. By way of example, cavity 22 can be filled with liquid antibiotics or drugs for reducing intraocular pressure. An aperture 26 such as that shown through lens member 14 can be used to control the transfer of fluid from cavity 22 to the eye. The rate of fluid exchange can be controlled by the size of aperture 26. Alternatively, fluid transfer from cavity 22 would also occur if lens members 12 or 14 were fabricated from hydrophilic materials. The index of refraction of the fluid material 24 within cavity 22 should be maintained at a constant value during fluid transfers to facilitate the optimal operation of zone plate 16. This can be accomplished by initially filling cavity 22 with fluids having an index of refraction close to that of the eye fluids which will replace those flowing out of the cavity.

Lens elements 12 and 14 can be produced directly in a replication process (e.g. injection molding). Alternatively, lens elements 12 and 14 can be machined or otherwise formed from lens blanks. Although both lens members 12 and 14 have convex outer surfaces OS in the embodiments shown, either or both could also have concave or planar surfaces depending upon the refractive optical contribution desired from the lens member. Similarly, inner surfaces IS could be planar or convex. Edges E can be mated together either before or after outer surfaces OS are shaped to the desired form. Liquid materials 24 can be injected into cavity 22 after lens elements 12 and 14 have been mated together. Alternatively, cavity 22 can be maintained full of the liquid or solid material 24 while lens members 12 and 14 are affixed. Lens members 12 and 14 can also be multilayer members. Ultrasonic welding techniques for manufacturing lenses such as 10 are described in greater detail in subsequent portions of this specification.

Lenses such as 10 have considerable advantages over those of the prior art. Since diffractive zone plate 16 is within lens 10 and not on outer surfaces OS, it is not subject to common problems associated with inorganic materials, protein deposits and other debris which tend to accumulate on structures of this type when exposed to portions of the human eye. Erosions and abrasion of cornea tissue are also prevented. Transferring medicinal substances 24 in cavity 22 to the eye or eye cavity is a convenient method for eliminating steps which may otherwise have to be performed by medical personnel or the patient. The above-described structures thereby facilitate healing following surgical procedures, and help prevent disease or other complications associated with the eye.

Figure 3:
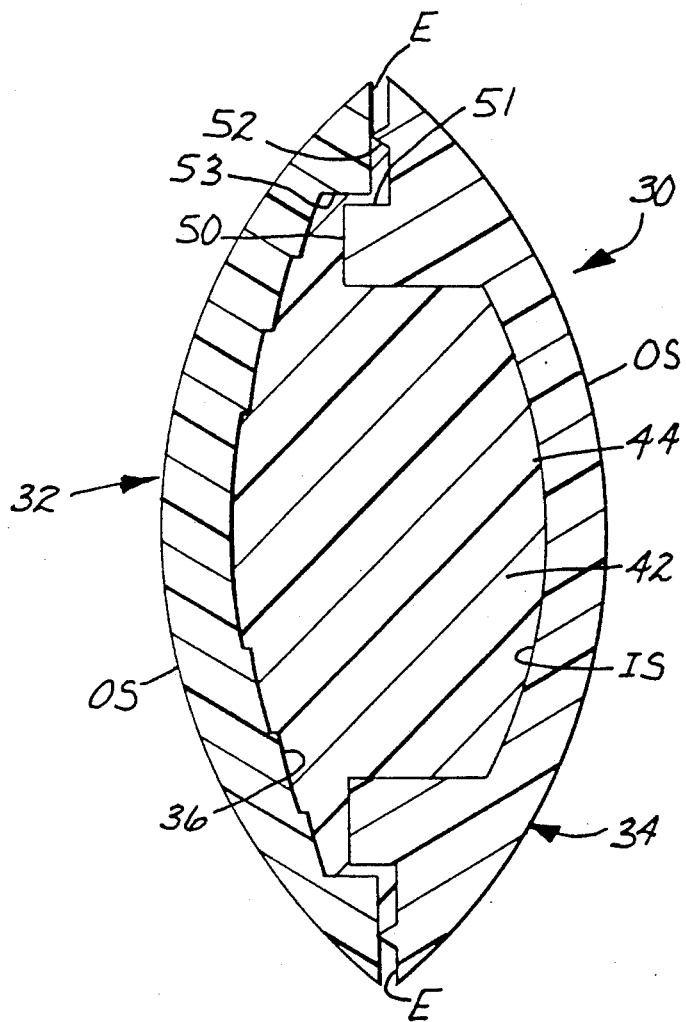
FIG. 3 is a sectional view of a second embodiment of an ophthalmic lens in accordance with the present invention.

Another embodiment of the present invention, ophthalmic lens 30, can be described with reference to FIGS. 3 and 4. Like ophthalmic lens 10 described above, lens 30 includes first and second lens members 32 and 34 which have inner surfaces IS and outer surfaces OS. Inner surface IS of lens member 32 includes a multifocal diffractive zone plate 36. Annular edges E of lens members 32 and 34 are joined together to form a cavity 42 adjacent zone plate 36. Cavity 42 can be injected or otherwise filled with a substance 44. With the exception of edges E and the method by which these edges are bonded together, other elements and characteristics of ophthalmic lens 30 can be identical to corresponding elements of lens 10 described above.

Edges E of lens members 32 and 34 are configured to be welded together through exposure to ultrasonic energy. To facilitate this welding process, edge E of one of the lens members (e.g. lens member 34 in FIGS. 3 and 4) includes projection 50 and a tapered energy director 52. Projection 50 is annular in the embodiment shown, and extends around edge E. Projection 50 is configured to extend into lens member 32 adjacent its edge E and functions as a guide to align the two lens members. Annular energy director 52 extends around lens member 34 from its edge E, and is positioned so as to be adjacent edge E of lens member 32. In the embodiment shown, energy director 52 is triangular in cross section. The angle formed between the side walls and base of energy director 52 is approximately 60° in one embodiment, but can vary (e.g. over a range of 45°–70°). The height and width of energy director 52 can also vary. Heights in the range of 0.005 inch to 0.009 inch (0.127 to 0.229 millimeter) have been found to work well, as have widths of 0.005 to 0.015 inch (0.127 to 0.381 mm). Energy director 52 directs ultrasonic energy to the point at which director 52 meets lens member 32 to facilitate a quality bond between the two lens members.

The gap between outside edge 51 of projection 50 and the adjacent surface 53 of lens member 32 functions as a flash trap for receiving molten material from energy director 52 during the ultrasonic welding operation, and for preventing this material from flowing into cavity 42. This gap should be wide enough to permit projection 50 to fit within lens member 32 without deforming either of lens members 32 and 34, and to permit molten material from energy director 52 to flow therein and seal the gap. If the gap is too large, it will not be filled in by the molten material and may be visible. Gaps in the range of 0.005–0.007 inch (0.127 to 0.178 mm) have been found to work well.

Figure 4:
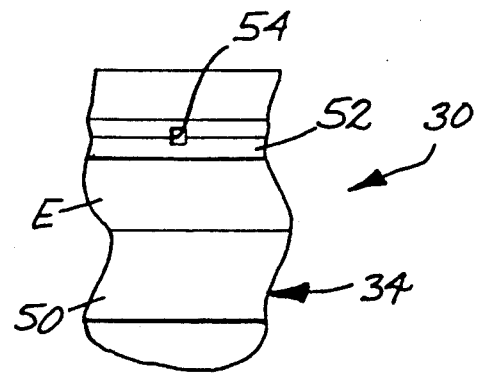
FIG. 4 is a detailed view of a portion of the edge of the lens shown in FIG. 3.

As shown in FIG. 4, one or more transversely oriented slots 54 (only one is shown) can extend across energy director 52. Slots 54 can be adapted to serve the same function as hole 26 of lens 10, that being to facilitate the transfer of liquid substances 44 between lens cavity 42 and the eye or eye cavity (not shown). Slots 54 also function as vents for the evacuation of air when viscous materials such as ACMAS which are placed in cavity 42 spread to the edges of the cavity during welding. Ophthalmic lens 30 has all the advantages of lens 10 described above. In addition to being effective, ultrasonic bonding prevents optical distortion of lens members 32 and 34.

Figure 5:
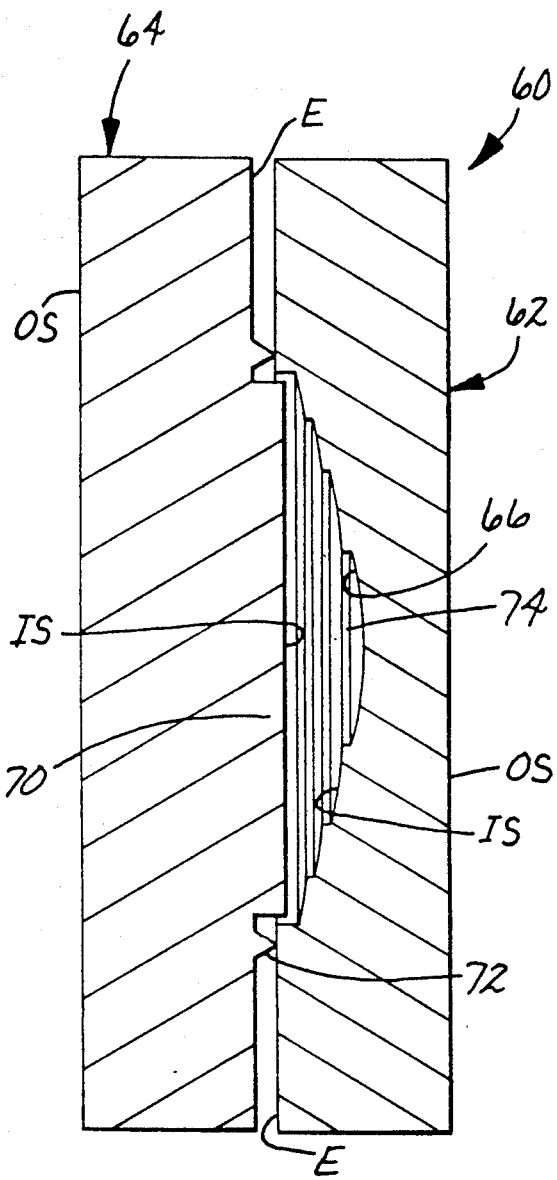
FIG. 5 is an illustration of a precursor lens assembly in accordance with the present invention and from which a lens such as that shown in FIG. 3 can be fabricated.

A precursor lens assembly 60 in accordance with the present invention is illustrated generally in FIG. 5. Assembly 60 includes unfinished lens members 62 and 64. In the embodiment shown, inner surfaces IS of lens member 62 is generally concave. Inner surface IS of lens member 64 is planar and formed on a circular projection 70 which extends into lens member 62. A multifocal diffractive zone plate 66 is formed on inner surface IS of lens member 62. Annular bonding edge E of lens member 64 includes an energy director or tapered ridge 72 which mates with edge E of lens member 62. Ridge 72 can be identical to energy director 52 of lens 30 described above with reference to FIGS. 3 and 4. Once lens members 62 and 64 have been bonded together at their edges E, the outer surfaces OS can be finished to patient specifications by grinding or other known machining processes. Haptics such as those shown at 18 in FIG. 1 can also be machined from lens members 62 and 64. A cavity 74 in precursor lens assembly 60 can be filled with a substance (not shown) of the type and in the manner of those described above with reference to lenses 10 and 30. Lens elements 62 and 64 can also be bonded to one another using adhesive or other welding techniques such as those described with reference to lens 10. In addition to having the advantages of lenses 10 and 30, the precursor lens assemblies such as 60 can be kept in stock and machined to required specifications as needed.

Figure 6:
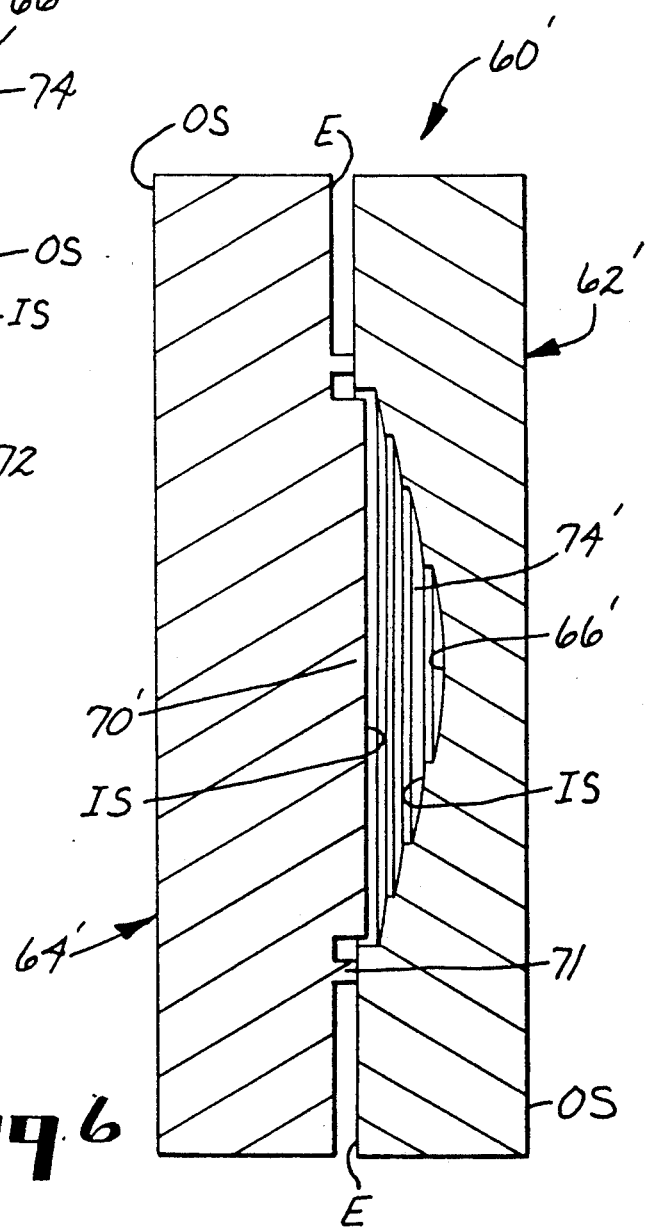
FIG. 6 is an illustration of another embodiment of a precursor lens assembly in accordance with the present invention.

Another precursor lens assembly is designated by reference numeral 60' and illustrated in FIG. 6. Lens assembly 60' is configured for assembly using ultrasonic welding techniques. With the exception of energy director 71, all other features of lens assembly 60' can be identical to corresponding features of lens assembly 60 described above with reference to FIG. 5, and are designated with corresponding but primed (e.g., ') reference characters. Annular energy director 71 extends around edge E of lens member 64' and has a smooth upper edge surface of extended width configured to mate with the edge E of lens member 62'. In the embodiment shown, energy director 71 is rectangular in cross-section and has a flat upper edge surface. The height of energy director 71 can vary between 0.127 and 0.229 millimeter, while the width can vary between 0.127 and 0.381 millimeter. Ophthalmic lens members such as 62' and 64' which are manufactured from hydrogel materials and include an energy director 71 can be securely welded together using the ultrasonic bonding techniques described below.

Figure 7:
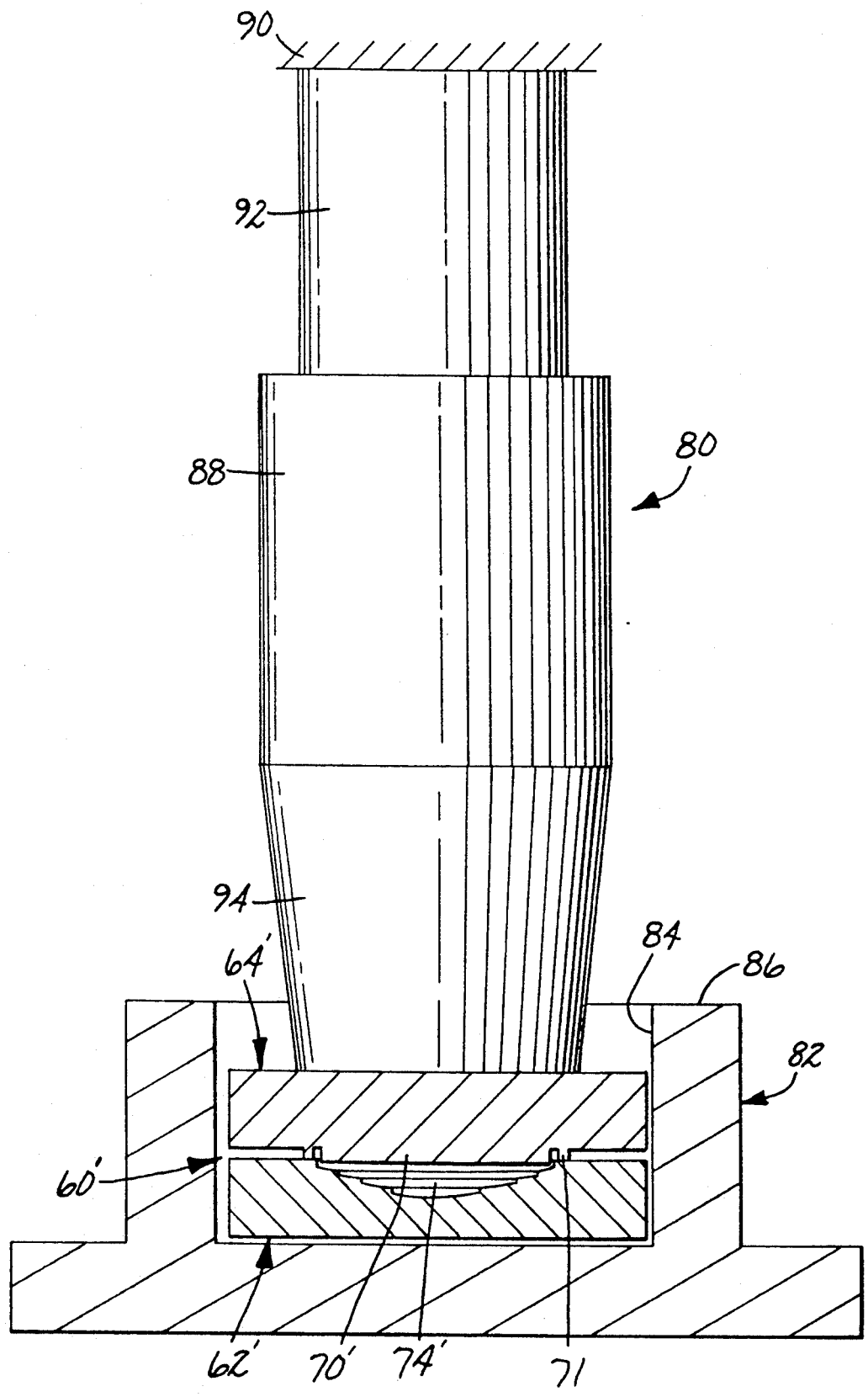
FIG. 7 is an illustration of a fixture and ultrasonic welder which can be used to ultrasonically assemble the precursor lens assembly shown in FIGS. 5 and 6.

The individual lens members of lenses 12 and 30 and precursor lens assemblies 60 and 60' can be securely and efficiently joined using the ultrasonic welder 80 and fixture 82 illustrated in FIG. 7. For purposes of illustration only, lens assembly 60' is shown in FIG. 7. Fixture 82 includes a well 84 formed by one or more walls 86. Well 84 is sized to firmly seat lens assembly 60, yet permit the lens assembly to be inserted into and removed from the well without substantial deformation. The individual lens members (e.g., 62, 64 and 62', 64') should be well cleaned and free of debris before they are welded using the procedures described below.

In one embodiment, ultrasonic welder 80 is a Branson Model 4AE welder. This welder 80 includes a booster 88 which is movably mounted with respect to a base 90 by an air cylinder 92. Ultrasonic energy produced by booster 88 is coupled to lens assembly 60' by horn 94. The pressure applied to lens assembly 60 through horn 94 is controlled by air cylinder 92. Air cylinder 92 must be capable of exerting enough pressure to permit high quality bonding of lens members 62' and 64'. Too much pressure, on the other hand, can result in overwelding and destroy the bond. Pressure settings obtainable from a 1.00–1.25 inch (25.4–31.75 mm) cylinder 92 have been found to work well. A silver booster 88 which generates ultrasonic energy at a frequency of 40 KHz is preferably used to weld lens members such as 62' and 64', including those fabricated from PMMA and hydrogels. Horns 94 having a diameter equal to or greater than the diameter of the energy director of the lens member being welded (e.g., energy director 71 of lens member 64') have been found to result in the strongest and highest quality bond.

A preferred method of using ultrasonic welder 80 and fixture 82 to ultrasonically weld PMMA lens members such as 62 and 64 which have a thickness of 2.5 mm and an air filled cavity 74 is described immediately below. The energy director 72 of these PMMA lens members 62 and 64 preferably have a triangular cross-section and 0.005 inch (0.127 mm) height. After being preheated to a temperature of 100°–120° F. (37.8–48.9° C.) over a period of forty-five minutes and positioned in well 84, horn 94 is forced into physical contact with lens member 64 at a pressure in the range of 50–75 PSIG (344.9 K to 517.1 KN/m$^2$). The pressure used in one preferred embodiment is 60 PSIG (413.7 KN/m$^2$). Booster 88 is then activated for a weld time during which the energy monitored on the end of the booster adjacent horn 94 reaches a peak of 140–150 Joules. Weld times in the range of 0.180.30 seconds have been found to work well, with 0.20 second being optimum. Following the termination of this weld period, ultrasonic welder 80 remains forced into contact with lens assembly 60 for a hold period in the range of 0.25 to 0.40 second, and preferably 0.30 second. These procedures have been found to produce a high quality joint between PMMA lens members 62 and 64. Joints of this type are, if at all, barely visible under a 50×microscope, and require at least ten pounds of force or 44.5 Newtons (e.g., as measured by an Instron rheometer) to be broken.

When welding PMMA lens members 62 and 64 to form a lens assembly 60 having a cavity 74 filled with saline solution, it is advantageous to used degassed saline to reduce the amount of air or other gases which might otherwise become entrapped within the cavity. In a preferred embodiment of the PMMA lens assembly such as 60 having a saline filled cavity 74, energy director 72 has a height of 0.008 inch (0.203 mm). Initially, well 84 is partially filled with degassed saline. A lower lens member (e.g., 62) is then placed in well 84 and moved around to enable any gases trapped on its surface to escape. After additional saline is added to well 84, an upper lens member (e.g., 64) is positioned on top of lower lens member 62 in such a manner as to prevent air from being entrapped within cavity 74. Upper lens member 64 can then be shifted around to evacuate any air or other entrapped gases.

Lens member 64 used in conjunction with the lens assembly 60 having a saline filled cavity 74 preferably has an energy director with a height of 0.008 inch (0.203 mm). To enable optimum welding, lens members 62 and 64 should be preheated to a temperature between 90° and 100° F. (32.2–37.8° C.) for a period of one hour, and subjected to a force of 100 PSIG (689.5 KN/m$^2$) during welding. Other forces in the 90–115 PSIG (620.6 K–792.9 KN/m$^2$) range have also been found to work well. Weld periods in the range 0.25 to 0.35 second have been found to work well, with 0.30 second being optimum. During the weld period the peak energy monitored at booster 88 should reach a level of 180–220 Joules. Following the weld period, lens assembly 60 should be kept under pressure for a hold period in the range of 0.30 to 0.40 second, and preferably 0.35 second. A PMMA lens assembly such as 60 having a saline filled cavity 74 and manufactured in accordance with the above-described conditions has been found to have a high quality bond between its lens members 62 and 64.

A preferred method for ultrasonically welding PMMA lens members 62 and 64 to form a lens assembly 60 having a cavity 74 filled with inert materials such as ACMAS and MACMAS includes preheating the lens members to a temperature of 100°–120° F. (37.7°–48.9° C.) over a period of forty-five minutes before positioning them within well 84. ACMAS and MACMAS materials are relatively viscous, and should be degassed prior to use. After lens member 62 has been positioned within well 84, a syringe can be used to place a sufficient volume of the inert material on the inner surface IS of the lens member. Lens member 64 can then be placed on lens member 62 in such a manner as to cause the inert material to spread throughout cavity 74. It is desirable to place only as much material on the inner surface IS of lens member 62 as is necessary to fill cavity 74. An energy director having a height of 0.007–0.009 inch (0.178–0.229 mm) will facilitate a quality bond even if too much inert material was placed on the lens member and was spread beyond the energy director. Following the procedures described above, a high quality bond can be formed between lens members 62 and 64 with a pressure setting of 65–75 PSIG (448.2 to 517.1 KN/m$^2$), a weld time of 0.20–0.27 second, a peak energy of 100–115 Joules and a hold time of 0.25–0.40 second. Optimum bond conditions have been achieved using a pressure setting of 70 PSIG (482.6 KN/m$^2$), a weld period of 0.23 second, a peak energy of 110 Joules, and a hold period of 0.30 second.

Surprisingly, it has been found that hydrogel lens members such as 62' and 64' having an equilibrium moisture content greater than 25.0% can be bonded using a welder 80 and fixture 82 of the type shown in FIG. 7. Lens members 62' and 64') manufactured from commercially available HEMA hydrogels from Bausch & Lomb and Hydron having an equilibrium moisture content of 38.5% have been bonded using this equipment. Perhaps even more surprisingly, hydrogel lens members such as 62' and 64' having an equilibrium moisture content greater than 55% can be bonded using welder 80 and fixture 82. For example, lens members 62' and 64' manufactured from hydrogel material disclosed in the Tahan U.K. patent publication 2,171,106 and having an equilibrium moisture content of 61.0% have been securely bonded using this equipment.

A preferred approach involves the use of hydrogel lens members 62' and 64' which are 2.0 mm in thickness, with one of the lens members having an energy director 71 of generally rectangular cross-section. Energy director 71 can have a height of 0.005–0.007 inch (0.127–0.178 mm) and width of 0.005–0.015 inch (0.127–0.381 mm). Hydrogel lens members 62 and 64 are positioned within well 84 at room temperature (e.g., 65° F.–80° F. or 18.3°–26.7° C.). Air cylinder 92 is set to apply a pressure of 8 to 10 PSIG (55.1 K–68.9 KN/m )

onto lens member 64' through booster 88 and horn 94. A high quality bond between lens members 62' and 64' can be attained using a weld period 0.15-0.22 second to achieve a peak energy of 10-25 Joules, followed by a hold period of 0.15-0.25 second. Optimum bond conditions have been achieved with a weld period of 0.17 second and a hold period of 0.20 second.

Although the present invention has been described with reference to preferred embodiments, workers skilled in the art will recognize that changes may be made in form and detail without departing from the spirit and scope of the invention. By way of example, ophthalmic lenses in accordance with the present invention can be embodied as contact lenses, intraocular lenses, artificial corneas and intralamellar implants.

What is claimed is:

1. A multifocal intraocular lens including:
   a first lens member having a smooth outer surface and an inner surface with a multifocal diffractive zone plate and an edge about its perimeter, the diffractive zone plate formed from material characterized by an index of refraction and imparting multifocal diffractive optical power to the lens;
   a second lens member formed from material characterized by an index of refraction and having a smooth outer surface and an inner surface with an edge about its perimeter, the edge of the second lens member fixedly jointed to the edge of the first lens member;
   a cavity defined by the inner surfaces of the first and second lens members adjacent the zone plate;
   a solid or fluid material within the cavity characterized by an index of refraction which is different than the index of refraction of the zone plate; and
   a curved outer surface on at least one of the first and second lens members, for imparting refractive optical power to the lens.

2. The lens of claim 1 and including a weld joining the edges of the first and second lens members.

3. The lens of claim 2 and including an ultrasonic weld joining the edges of the first and second lens members.

4. The lens of claim 3 wherein the edge of one of the first and second lens members includes an energy director in contact with the edge of the other lens member.

5. The lens of claim 3 wherein at least one of the first and second lens members includes a guide projection for extending into the other lens member.

6. The lens of claim 1 and including adhesive joining the edges of the first and second lens members.

7. The lens of claim 1 and including air within the cavity.

8. The lens of claim 1 and including liquid material within the cavity.

9. The lens of claim 8 and further including a fluid transport mechanism for permitting fluid transfer between the cavity and an exterior surface of the lens.

10. The lens of claim 9 wherein the fluid transport mechanism includes an aperture through at least one of the first and second lens members.

11. The lens of claim 9 wherein at least one of the first and second lens members is formed from a hydrophilic material which functions as the fluid transport mechanism.

12. The lens of claim 9 and including liquid medication within the cavity.

13. The lens of claim 1 wherein at least one of the first and second lens members includes a concave inner surface.

14. The lens of claim 1 and further including a curved surface on both the first and second lens members for imparting refractive optical power to the lens.

15. A multifocal intraocular lens precursor assembly for fabrication of a finished lens, including:
    a first unfinished lens member having a thickness, an inner surface with an edge and a multifocal diffractive zone plate on the inner surface, the diffractive zone plate formed from material characterized by an index of refraction and imparting multifocal diffractive optical power to the finished lens;
    a second unfinished lens member having a thickness and an inner surface with an edge, the edge of the second lens member fixedly joined to the edge of the first lens member;
    a cavity defined by the inner surfaces of the first and second lens members adjacent the zone plate;
    a solid or fluid material within the cavity characterized by an index of refraction which is different than the index of refraction of the zone plate; and
    sufficient thickness on at least one of the first and second lens members to enable the fabrication of a smooth, curved outer surface on the lens member to impart refractive optical power to the finished lens.

16. The precursor lens assembly of claim 15 and including a liquid substance within the cavity.

17. The precursor lens assembly of claim 16 and further including:
    a liquid medication within the cavity; and
    a fluid transport mechanism for causing fluid transfer between the cavity and an exterior surface of the lens.

18. The precursor lens assembly of claim 15 and further including sufficient thickness on both the first and second lens members to enable the fabrication of smooth, curved outer surfaces on the lens members to impart refractive optical power to the finished lens.

19. A multifocal intraocular lens, including:
    a first lens member having a smooth outer surface and an inner surface with an edge about its perimeter and a multifocal diffractive zone plate, the diffractive zone plate characterized by an index of refraction and imparting multifocal diffractive optical power to the lens;
    a second lens member having a smooth outer surface and an inner surface with an edge about its perimeter, the edge of the second lens member fixedly joined to the edge of the first lens member;
    a curved outer surface on at least one of the first and second lens members, for imparting refractive optical power to the lens;
    a cavity adjacent the zone plate and defined by the inner surfaces of the first and second lens members; and
    a material within the cavity which is characterized by an index of refraction which is different than the index of refraction of the diffractive zone plate.

20. The lens of claim 19 and further including a solid material within the cavity.

21. The lens of claim 19 and further including a liquid material within the cavity.

22. The lens of claim 22 and further including:
    a liquid medication within the cavity; and a fluid transport mechanism for causing fluid transfer between the cavity and an exterior surface of the lens.

23. The lens of claim 19 and further including a curved outer surface on both the first and second lens members, for imparting refractive optical power to the lens.

24. A multifocal intraocular ophthalmic lens, including:
- a lens having first and second smooth and opposed outer surfaces;
- a multifocal diffractive zone plate characterized by an index of refraction within the lens between the outer surfaces, for imparting multifocal diffractive optical power to the lens;
- a region of solid or fluid material characterized by an index of refraction which is different than the index of refraction of the zone plate, the region of material within the lens between the outer surfaces and in contact with the zone plate; and
- a curved outer surface on at least one of th first and second opposed outer surfaces, for imparting refractive optical power to the lens.

25. The ophthalmic lens of claim 24 and including:
- a liquid medication within the region and adjacent the zone plate; and
- a fluid transport mechanism for causing fluid transfer between the region and the outer surface of the lens.

26. The ophthalmic lens of claim 25 wherein the fluid transport mechanism includes an aperture coupling the outer surface to the region.

27. The ophthalmic lens of claim 24 and further including a curved surface on both the first and second opposed outer surfaces, for imparting refractive optical power to the lens.

28. A method for manufacturing a multifocal intraocular lens, including:
- providing first and second lens members having outer surfaces and inner surfaces with edges about the perimeters, at least one of the lens members having a concave inner surface, at least one of the lens members having a multifocal diffractive zone plate characterized by an index of refraction on the inner surface for imparting diffractive multifocal optical power to the lens, and at least one of the lens members having a curved outer surface for imparting refractive optical power to the lens;
- joining the first and second lens members at their edges to form a cavity adjacent the zone plate defined by the inner surfaces of the first and second lens members; and
- filling the cavity with material characterized by an index of refraction which is different than the index of refraction of the multifocal diffractive zone plate.

29. The method of claim 28 wherein filling the cavity includes filling the cavity with a solid substance.

30. The method of claim 28 wherein filling the cavity includes filling the cavity with a fluid substance.

31. The method of claim 30 wherein:
- filling the cavity includes filling the cavity with a curable liquid substance; and
- the method further includes curing the liquid in the cavity.

32. The method of claim 30 wherein filling the cavity includes filling the cavity with a liquid medicinal substance.

33. The method of claim 28 wherein joining the lens members includes welding the edges of the lens members together.

34. The method of claim 33 wherein welding the edges together includes ultrasonically welding the edges together.

35. The method of claim 28 wherein providing first and second lens members includes providing first and second lens members which have curved outer surfaces for imparting refractive optical power to the lens.

* * * * *